United States Patent [19]

Miyazawa et al.

[11] 4,002,631
[45] Jan. 11, 1977

[54] TETRAHYDROQUINOLINE OR JUJOLIDINE DERIVATIVE OF A LACTONE COMPOUND OF PYRIDINE-CARBOXYLIC ACID

[75] Inventors: Yoshihide Miyazawa; Minoru Ozutsumi; Satoshi Ogawa, all of Tokyo, Japan

[73] Assignee: Hodogaya Chemical Co., Ltd., Tokyo, Japan

[22] Filed: July 24, 1974

[21] Appl. No.: 491,435

[30] Foreign Application Priority Data

July 24, 1973   Japan ............................ 48-82649

[52] U.S. Cl. ...................... 260/287 T; 260/243 AE; 260/247.2 B; 260/247.2 R; 260/268 BQ; 260/268 TR; 260/279 R; 260/294.9; 260/295 F; 260/295 T; 260/295.5 B; 260/295.5 T; 260/295.5 R; 260/295 R; 428/411

[51] Int. Cl.² ............. C07D 405/14; C07D 471/06

[58] Field of Search ..... 260/287 T, 287 CE, 287 P, 260/268 TR, 268 BQ, 247.2 B

[56] References Cited

UNITED STATES PATENTS 3,916,070   10/1975   Ozutsumi et al. ............. 260/287 T

*Primary Examiner*—Donald G. Daus
*Assistant Examiner*—David E. Wheeler
*Attorney, Agent, or Firm*—Sughrue, Rothwell, Mion, Zinn & Macpeak

[57] ABSTRACT

A lactone compound represented by the following formula

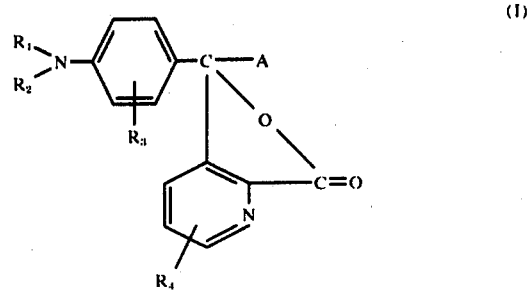

(I)

or

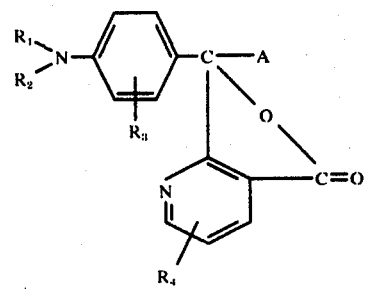

or a mixture thereof, wherein $R_1$, $R_2$, $R_3$, $R_4$ and A are as defined hereinafter and a process for preparing the same are disclosed.

3 Claims, No Drawings

TETRAHYDROQUINOLINE OR JUJOLIDINE DERIVATIVE OF A LACTONE COMPOUND OF PYRIDINE-CARBOXYLIC ACID

BACKGROUND OF THE INVENTION

1. Field of the Invention

This invention relates to novel marking color formers useful for recording materials such as heat-sensitive copying paper, hectographic printing papers, pressure-sensitive copying papers, etc., and the process for preparing the same. More particularly, this invention relates to novel lactone compounds of pyridine-carboxylic acids and the process for preparing the same.

SUMMARY OF THE INVENTION

An object of this invention is to provide novel pyridine-carboxylic acid lactones represented by the formula (I)

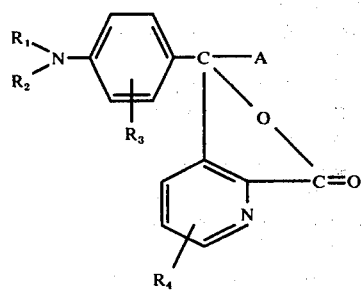

(I)

or

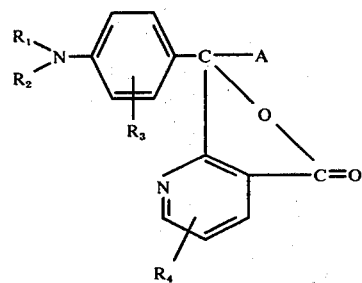

or a mixture thereof, wherein $R_1$ and $R_2$ each represents a hydrogen atom, an acyl group, a lower alkyl group which may be substituted with a halogen atom, a cyano, hydroxyl, lower alkoxy, lower alkylamino, acetyl or phenoxy group, or a benzyl or phenyl group which may be substituted with a lower alkyl group, a halogen atom, a lower alkoxy, nitro, amino or lower alkylamino group, or $R_1$ and $R_2$ may, when taken together with a nitrogen atom to which $R_1$ and $R_2$ are attached, form a part of a saturated hydrocarbon chain of a heterocyclic ring; $R_3$ represents a hydrogen or halogen atom, a nitro, amino, lower alkylamino group or a lower alkyl group which may be substituted with a halogen atom or a lower alkoxy group, a lower alkoxy group which may be substituted with a halogen atom, or a benzyl, benzyloxy or phenoxy group which may be substituted with a halogen atom, a lower alkyl, alkoxy or lower alkylamino group; $R_4$ represents a hydrogen or halogen atom, a lower alkyl group or a phenyl group; and A represents a carbazolyl, acridinyl, phenothiazinyl, thienyl, thianaphthenyl, morpholinophenyl, julolidinyl or tetrahydroquinolyl group which may be substituted with a lower alkyl, lower alkylamino, acyl or nitro group; the alkyl moiety in said lower alkyl, lower alkoxy or lower alkylamino group containing 1 to 5 carbon atoms. The lactone compounds of this invention are useful as color formers.

DETAILED DESCRIPTION OF THE INVENTION

The lactone color formers of this invention represented by the above formula (I) can be prepared by the following alternative procedures:

1. Condensation of a benzoyl pyridine-carboxylic acid represented by the formula (II)

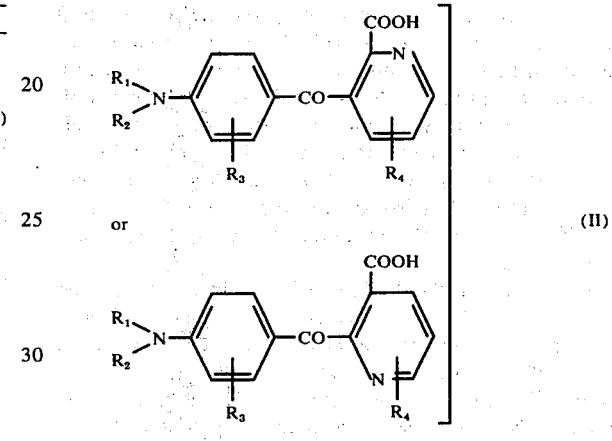

(II)

or a mixture thereof, wherein $R_1$, $R_2$, $R_3$ and $R_4$ are as defined above with a heterocyclic compound of the formula (III)

$$A - H \qquad (III).$$

wherein A is as defined above followed by treating the reaction product with an alkali.

2. Condensation of a (heterocyclic-carbonyl)-pyridine-carboxylic acid represented by the formula (IV)

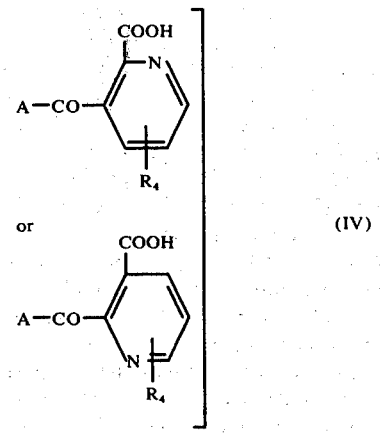

(IV)

or a mixture thereof, wherein $R_4$ and A are as defined above with an aniline compound represented by the formula (V)

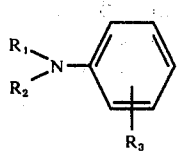

(V)

wherein $R_1$, $R_2$ and $R_3$ are as defined above followed by treating the reaction product with an alkali.

The novel color former of the present invention is an essentially colorless or slightly colored powder which is stable in the atmosphere but undergoes changes in color to red, purple, blue or green on heating. The lactones of this invention as color formers are soluble in or miscible with natural or synthetic high molecular weight substances such as animal, vegetable or mineral waxes, ethyl cellulose, polyvinyl acetate, rosin-modified alkyd resins, etc., and are soluble in a wide variety of organic liquids such as alcohols, e.g., methanol, ethanol, butanol, etc., cellosolve ethers, e.g., ethyl cellosolve, etc., hydrocarbons, e.g., benzene, toluene, alkylnaphthylenes, dibenzylbenzene, dibenzyltoluene, etc., halogenated hydrocarbons, e.g., chloroform, chlorobenzenes, tetrachloroethane, etc., trioctylphosphate and the like.

A solution of the lactone of this invention in the above organic liquid develops a wide variety of hues from red to green color immediately after the solution is adsorbed on active clay substances such as acid clay, attapulgite, zeolite, bentonite and the like, solid organic acids such as succinic acid, maleic acid, tannic acid, benzoic acid and the like, or acidic polymers such as carboxypolyethylene, phenol-aldehyde polymers, styrenemaleic anhydride copolymers containing residual acidic groups, and the like. The colors developed on such solid materials generally have a high color density and superior in terms of light-fastness, water resistance and sublimation properties in comparison with those obtained by the conventionally known color formers such as triarylmethane lactones, e.g., crystal violet lactone, and malachite green lactone, xanthene lactam or lactone, e.g., rhodamine lactam and 3-diethylamino-7-anilino-fluoran, 3,3-bis-diethylaminophenyl-4 (or 7) -azaphthalide and the like.

Typical examples of the benzoyl-pyridine-carboxylic acids represented by the formula (II) which can be used in this invention as a starting for the production of the lactones (I) are 3(or 2)-(4'-aminobenzoyl)-pyridine-carboxylic acid -(2) [or (3)], 3 (on 2)-(4'-acetamidobenzoyl)-pyridine-carboxylic acid -2 [or (3)], 3 (or 2)-(4'-benzamido-benzoyl)-pyridine-carboxylic acid -(2) [or (3)], 3(or 2) - (4'-methylaminobenzoyl)-pyridine-carboxylic acid-(2) [or (3)], 3(or 2)-(4'-dimethylaminobenzoyl)-pyridine-carboxylic acid-(2) [or (3)], 3(or 2)-(4'β-chloroethylaminobenzoyl)-pyridine-carboxylic acid -(2) [or (3)], 3 (or 2)-[4'-(N-chloroethyl-N-ethyl)-aminobenzoyl]-pyridine-carboxylic acid-(2) [or (3)], 3(or 2)-[4'-(N-β-cyanoethyl-N-ethyl)-aminobenzoyl]-pyridine-carboxylic acid-(2) [or (3)], 3(or 2)-[4'-(N-ethoxyethyl-N-ethyl)-aminobenzoyl]-pyridine-carboxylic acid-(2) [or (3)], 3(or 2)-[4'-N,N,-di-β-chloroethyl)-aminobenzoyl]-pyridine-carboxylic acid-(2) [or (3)], 3(or 2)-[4'-N-β-oxyethylaminobenzoyl]-pyridine-carboxylic acid-(2) [or (3)], 3(or 2)-[4'-(N-β-oxyethyl-N-Methyl) -aminobenzoyl]-pyridine-carboxylic acid-(2) [or (3)], 3(or 2)-[4'-N-(N-β-oxyethyl-N-β-cyanoethyl)-aminobenzoyl]-pyridine-carboxylic acid-(2) [or (3)], 3(or 2)-[4'-(N-β-dimethylaminoethyl)-aminobenzoyl]-pyridine-carboxylic acid-(2) [or (3)], 3(or 2)-(4'-N-acetonylaminobenzoyl)-pyridine-carboxylic acid-(2) [or (3)], 3(or 2)-[4'-(N-benzyl-N-methyl)-aminobenzoyl]-pyridine-carboxylic acid-2[or (3)], 3(or 2)-(4'-dibenzylaminobenzoyl)-pyridine-carboxylic acid-2[or(3)], 3(or 2)-[4'-(N-4''-methylbenzyl-N -ethyl)-aminobenzoyl]- pyridine-carboxylic acid -(2) [or (3)], 3 (or 2)-[4'-(N-4''-aminobenzyl-N-ethyl)-amino-benzoyl]-pyridine-carboxylic acid-2[or (3)], 3 (or 2)-[4'-(N-4''-nitrobenzyl-N-ethyl)-aminobenzoyl]-pyridine-carboxylic acid-(2)[or (3)], 3(or 2)-(4'-phenylaminobenzoyl)-pyridine-carboxylic acid-(2) [or (3)], 3(or 2)-[4'-(N-phenyl-N-methyl)-aminobenzoyl]-pyridine-carboxylic acid-(2) [or (3)], 3(or 2)-[4'-(N-4''-chlorophenyl-N-methyl)-aminobenzoyl]-pyridine-carboxylic acid-(2) [or (3)], 3(or 2)-[4'-(N-4''-methylphenyl)-aminobenzoyl]-pyridine-carboxylic acid-(2) [or (3)], 3(or 2)-[4'-(N-4''-methylphenyl-N-methyl) -aminobenzoyl]-pyridine-carboxylic acid -(2) [or (3)], 3(or 2)-[4'-(N-4'''-ethoxyphenyl)-aminobenzoyl]-pyridine-carboxylic acid-(2) [or(3)], 3(or 2)-[4'-(N-4''-ethoxyphenyl-N-methyl)-aminobenzoyl]-pyridine-carboxylic acid-(2) [or (3)],3(or 2)-[4'-(N-benzyl -methyl)-amino-2'-methylbenzoyl]-pyridine-carboxylic acid-(2) [or (3)], 3 (or 2)-(4'-dibenzylamino-2'-methylbenzoyl)-pyridine-carboxylic acid-(2) [or (3)], 3(or 2)-(4'-ethylamino-2'-methylbenzoyl)-pyridine-carboxylic acid-(2) [or (3)], 3(or 2)-[4'-(N-β-cyanoethyl-N-ethyl)-amino-2'-methylbenzoyl]-pyridine-carboxylic acid-(2) [or (3)], 3(or 2)-[4'-N-β-cyanoethylamino-2'-methylbenzoyl)-pyridine-carboxylic acid-(2) [or (3)], 3(or 2)-(4'-diethylamino-2'-methylbenzoyl)-pyridine-carboxylic acid-(2) [or (3)], 3(or 2)-[4'-(N-β-ethoxyethyl-N-ethyl)-amino-2'-methylbenzoyl]-pyridine-carboxylic acid-(2)[or (3)], 3(or 2)-[4'-(N-β-cyanoethyl-N-β-oxyethyl)-amino-2'-methylbenzoyl]-pyridine-carboxylic acid-(2) [or (3)], 3(or 2)-[4'-(N-β-chloroethyl-N-ethyl)-amino-2'-methylbenzoyl]-pyridine-carboxylic acid -(2) [or (3)], 3(or 2)-[4'-benzyl-N- ethyl)-amino-2'-chlorobenzoyl]-pyridine-carboxylic acid-(2) [or (3)], 3(or 2)-[4'-(N-β-chloroethyl-N-ethyl)-amino-2'-nitrobenzoyl]-pyridine-carboxylic acid-(2) [or (3)],3(or 2)-[4'-(N-β-phenoxyethyl-N-ethyl)-amino-2'-methylbenzoyl]-pyridine-carboxylic acid-(2) [or (3)], 3(or 2)-[4'-(N-β-dimethylaminoethyl-N-ethyl)-amino-3'-methoxybenzoyl]-pyridine-carboxylic acid-(2) [or (3)], 3(or 2)-(4'-diethylamino-2'-trifluoromethylbenzoyl)-pyridine-carboxylic acid -(2) [or (3)], 3(or 2)-(4'-methylamino-2'-methoxybenzoyl)- pyridine-carboxylic acid-(2) [or (3)],3(or 2)-(4'-diethylamino-2'-ethoxy benzoyl)-pyridine-carboxylic acid-(2) [or (3)], 3(or 2) -[4'-(N-β-chloroethyl-N-ethyl)-amino-2'-ethoxybenzoyl]-pyridine-carboxylic acid-(2) [or (3)], 3(or 2)-(4'-dimethylamino-2'-methoxybenzoyl)-pyridine-carboxylic acid-(2) [or (3)], 3(or 2)-(4'-diethylamino-2'-chlorobenzoyl)-pyridine-carboxylic acid-(2) [or (3)],3(or 2)-(4'-diethylamino-2'-aminobenzoyl-pyridine-carboxylic acid-(2) [or (3)], 3(or 2)-(4'-diethylamino-2'-methylaminobenzoyl)-pyridine-carboxylic acid-(2) [or (3)], 3(or 2)-(4'-diethylamino-2'-dimethylaminobenzoyl)-pyridine-carboxylic acid-(2)[or (3)], 3(or 2)-(4'-diethylamino-2'-nitrobenzoyl)-pyridine-carboxylic acid-2-[or (3)], 3(or 2)-(4'-diethylamino-2'-methoxymethylbenzoyl)-pyridine-carboxylic acid-(2) [or (3)], 3(or 2)-(4'-diethylamino-2'-benzylbenzoyl)-pyridine-carboxylic acid-(2) [or (3)], 3(or 2)-[4'-diethylamino-2'(4''-methyl)-benzylbenzoyl]-pyridine-carboxylic acid-(2) [or (3)],3(or 2)-[4'-diethylamino-2'-(4''-chloro)-benzylbenzoyl)-pyridine-carboxylic acid-(2) [or (3)], 3(or 2)-[4'-dimethylamino-2'-(2''-ethoxy)-benzylbenzoyl]-pyridine-carboxylic acid-(2) [or (3)], 3(or 2)-[4'-dimethylamino-2'-(4''-dimethylamino)-benzylbenzoyl]-pyridine-carboxylic acid-(2) [or (3)], 3(or 2)-[4'-diethylamino-2'-β-chloroethoxybenzoyl-]-pyridine-carboxylic acid-(2) [or (3)], 3or 2)-[4'-diethylamino-2'-benzyloxybenzoyl]-pyridine-carboxylic acid-(2) [or (3)], 3(or 2) -[4'-diethylamino-2'-(4''-methyl)-benzyloxybenzoyl]-pyridine-carboxylic acid-2[or (3)], 3(or 2)-[4'-diethylamino-2'-phenoxybenzoyl]-pyridine-carboxylic acid- (2)[or (3)], 3(or 2)-[4'-dimethylamino-2'-(4''-chloro)-phenoxybenzoyl]-pyridine-carboxylic acid-(2) [or (3)], 3(or 2)-[4'-dimethylamino-2'-(4''-methylamino)-phenoxybenzoyl]-pyridine-carboxylic acid-(2)[or (3)], 3(or 2)-[4'-dimethylamino-2'-(4''-methoxy) phenoxybenzoyl]-pyridine-carboxylic acid-(2)[or (3)], 3(or 2)-(4'-morpholinobenzoyl)-pyridine-caboxylic acid-(2)[or (3)], 3(or 2)-(4'-pyrrolininobenzoyl)-pyridine-carboxylic acid-(2)[or (3)], 3(or 2)-(4'-piperazinobenzoyl)-pyridine-carboxylic acid-(2) [or (3)], 3(or 2)-(4'-piperidinobenzoyl)-pyridine-caboxylic acid -(2) [or (3)], 3(or 2)-(4'-dimethylaminobenzoyl)-4-chloropyridine -carboxylic acid-(2) [or (3)], 3(or 2)-(4'-dimethylaminobenzoyl)-4-methylpyridine-carboxylic acid-(2) [or (3)], 3(or 2)-)4'-diethylamino-2'-methylbenzoyl)-4-methylpyridine-carboxylic acid -(2) [or (3)], 3(or 2)-(4'-methylamino-2'-chlorobenzoyl)-4-methylpyridine-carboxylic acid-(2) [or (3)], 3(or 2)-(4'-dimethylamino-2'-methoxybenzoyl)-6-phenylpyridine-carboxylic acid-(2) [or (3)], 3(or 2)-(4'-(N-benzyl-N-methyl)-aminobenzoyl]-4-chloropyridine-carboxylic acid-(2) [or (3)], 3(or 2)-[4'-(N-4''-methylphenyl-N-methyl)-aminobenzoyl-9 -4-methyl-pyridine-carboxylic acid-(2) [or (3)], 3(or 2)-[4'-(N-4''-ethoxyphenyl-N-methyl)-aminobenzoyl]-6-phenyl-pyridine-carboxylic acid-(2) [or (3)], etc.

Representative examples of heterocyclic compounds represebted by the formula (III) which can be used in the present invention include carbazole, 9-ethylcarbazole, 3-nitro-9-ethyl-carbazole, acridine, phenothiazine, 10-methylphenothiazine, 10-acetylphenothiazine, 3-dimethylamino-10-methylphenothiazine, 3-nitro-10-methylphenothiazine, thiophene, thianaphthene, N-phenylmorpholine, julolidine, 1,2,3,4-tetrahydroquinoline, 1-methyl-2,3,4-trihydroquinoline and the like.

Representative examples of the (heterocyclic-carbonyl)-pyridine-carboxylic acids represented by the formula (IV) which can be used as starting materials for the production of the lactones (I) are 3(or 2)-[carbazole-carbonyl-(3')]-pyridine-carboxylic acid-(2) [or (3)], 3(or 2)-[9'-ethylcabazole-carbonyl-(3')]-pyridine-carboxylic acid-(2) [or (3)], 3(or 2)-[acridine carbonyl-(2')]-pyridine-carboxylic acid-(2) [or (3)], 3(or 2)-[phenothiazine-carbonyl-(3')]-pyridine-carboxylic acid-(2) [or (3)], 3(or 2)-[10'-methylphenothiazine-carbonyl-(3')]-pyridine-carboxylic acid-(2) [or (3)], 3(or 2)-[10'-acetylphenothiazine-carbonyl(-3')]-pyridine-carboxylic acid-(2) [or (3)], 3(or 2)-[7'-dimethylamino-10'-methylphenothiazine-carbonyl-(3')]-pyridine-carboxylic acid-(2) [or (3)], 3(or 2)-[7'-nitro-10'-methylphenothiazine-carbonyl-(3')]-pyridine-carboxylic acid-(2) [or (3)], 3(or 2)-[thenoyl-(2')]-pyridine-carboxylic acid-(2)[or (3), 3(or 2)-[thianaphtene-carbonyl-(2')]-pyridine-carboxylic acid-(2)[or (3)], 3(or 2)-[julolidine-carbonyl-(6')]-pyridine-carboxylic acid-(2) [or (3)], 3(or 2)-[1',2',-3',4'-tetrahydroquinoline-carbonyl-(6')]-pyridine-carboxylic acid-(2)[or (3)], 3(or 2)-[1'-methyl-2',3', 4'-trihydroquinoline-carbonyl-(6')]-pyridine-carboxylic acid-(2) [or (3)] and the like.

Representative examples of aniline compounds represented by the formula (V) which can be used in this invention are aniline, acetanilide, benzanilide, N-methylaniline, N-N-dimethylaniline, N-β-chloroethylaniline, N-β-chloroethyl-N-ethylaniline, N-β-cyanoethyl-N-ethylaniline, N-β-ethoxyethyl-N-ethylaniline, N-N-di-β-chloroethylaniline, N-β-oxyethylaniline N-β-oxyethyl-N-methylaniline, N-β-oxyethyl-N-β-cyanoethylaniline, N-β-dimethylaminoethylaniline, N-acetonylaniline, N-benzyl - N-methylaniline, N, N-di-benzylaniline, N-4'-methylbenzyl-N-ethylaniline, N-4'-aminobenzyl-N-ethylaniline, N-4'-nitrobenzyl-N-ethylaniline, diphenylamine, N-methyl-diphenylamine, N-methyl-N-4'-chlorophenylaniline, N-3'-methylphenylaniline, N-methyl-N-4'-methylphenylaniline, N-4'-ethoxyphenylaniline, N-methyl-N-4'-ethoxyphenylaniline, N-benzyl-N-methyl-3-methylaniline, N, N-dibenzyl -3-methylaniline, N-ethyl-3-methylaniline, N-β-cyanoethyl-N-ethyl-3-methylaniline, N-β-cyanoethyl-3-methylaniline, N, N-diethyl-3-methylaniline, N-β-ethoxyethyl-N-methyl-3-ethylaniline, N-β-cyanoethyl-N-β-oxyethyl-3-methylaniline, N-β-chloroethyl-N-ethyl-3-methylaniline, N-benzyl-N-ethyl-3-chloroaniline, N-β-chloroethyl-N-ethyl-3-nitroaniline, N-β-phenoxyethyl-N-ethyl-3-methylaniline, N-β-dimethylaminoethyl-N-ethyl-2-methoxyaniline, N, N-diethyl-3-trifluoromethylaniline, N-methyl-3-methoxyaniline, N-methyl-3-methoxyaniline, N, N-diethyl-3-ethoxyaniline, N-β-chloroethyl-N-ethyl-3-ethoxyaniline, N, N-dimethyl-3 -methoxyaniline, N, N-diethyl-3-chloroaniline, N-3'-diethylaminophenylaniline, N, N-diethyl-3-nitroaniline, N, N-diethyl-3-nitroaniline, N, N-diethyl-3-butoxyaniline, N,N-diethyl-3-benzylaniline, N, N-diethyl-3-(4'-methyl)-Benzylaniline, N, N-diethyl-3-(4'-chloro)-benzylaniline, N,N-dimethyl-3-(2'-ethoxy)-benzylaniline, N, N-dimethyl-3-(4'-dimethylamino)-benzylaniline, N, N-diethyl-3-(β-chloro)-ethoxyaniline, N, N-diethyl-3-benzyloxyaniline, N, N-diethyl-3-(4'-methyl)-benzyloxyaniline, N, N-diethyl-3-phenoxyaniline, N, N-dimethyl-3-(4'-methyl)-phenoxyaniline, N, N-dimethyl-3-(4'-chloro)-phenoxyaniline, N, N-dimethyl -3-(4'-methylaminol)-phenoxyaniline, N, N-dimethyl-3-(4'-methoxy)-phenoxyaniline, N-phenylmorpholine, N-phenylpyrrolidine, N-phenylpiperidine, N-phenylpiperazine, N-(3'-methyl)-phenylpiperidine and the like.

The benzoyl-pyridine carboxylic acids represented by the formula [II] and the (heterocyclic-carbonyl)-pyridine-carboxylic acids represented by the formula (IV) which can be used for producing the lactones of this invention can be prepared as follows:

About 1 mole of quinolinic anhydride represented by the formula

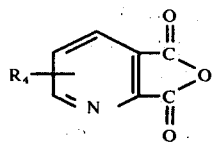

wherein R₄ is as defined in the formula (I) is reacted with about 1 to 2 moles of either an aniline compound represented by the formula (V) or a heterocyclic compound represented by the formula (III) in about 0.5 to 2.5 l of a volatile organic inert solvent such as carbon disulfide, tetrachloroethane, benzene, a chlorobenzene, a nitrobenzene and the like using about 1 to 3 moles of a Friedel-lCrafts catalyst such as zinc chloride, phosphorus chloride, aluminum chloride and the like at a temperature of from 10° to 110° C for a period of 1 to 9 hours. The reaction mixture is cooled to room temperature and the inert organic solvent is removed by decantation. The resulting reaction product is poured into 2 to 6 l of ice-water of cold dilute aqueous hydrochloric acid to hydrolyze the catalyst. The precipitated solid is filtered, washed successively with water and benzene and dried. There is obtained an isomer mixture comprising 3-benzoyl-pyridine-carboxylic acid-(2) and 2-benzyolpyridine-carboxylic acid-(3) represented by the formula (II) or an isomer mixture comprising 3-heterocyclic-carbonyl)-pyridine-carboxylic acid- (2) and 2-(heterocyclic-carbonyl)-pyridine-carboxylic acid -(3) represented by the formula (IV), respectively, as crystals. If necessary, the above obtained isomer mixture can be recrystallized to obtain each isomer.

The lactone color formers represented by the formula (I) can be prepared as follows. In the preparation of the lactone color formers, the pyridine-carboxylic acid used herein represented by the formula (II) or (IV) are those prepared as described above and two isomers of each pyridine-carboxylic acid may be present therein.

The color formers of pyridine-carboxylic acids (I) can be prepared by reacting either a (benzoyl)-pyridine-carboxylic acid represented by the formula (II) with a heterocyclic acompound represented by the formula (III) or a (heterocyclic-carbonyl)-pyridine carboxylic acid represented by the formula (IV) with an aniline compound represented by the formula (V) in the presence of a condensing agent. If desired, a volatile inert organic solvent such as chloroform, tetrachloroethane, benzene, chlorobenzenes or toluene can be employed as a solvent in order to ensure that the condensation reaction proceeds smoothly. Examples of condensing agents which can be used include concentrated sulfuric acid, acetic anhydride, phosphorus trichloride, phosphorus pentachloride, phosphorus oxychloride, phosphoric acid, polyphosphoric acid, zinc chloride, stannic chloride, aluminum chloride or the like, Of these condensing agents, concentrated sulfuric acid, acetic anhydride, polyphosphoric acid and the like are preferably employed because they can serve not only as a condensing agent but also as a reaction solvent. The process for prepating lactone color formers according to the present invention is illustrated below in detail.

1 mole of the benzoyl-pyridine-carboxylic acid (II) or the (heterocyclic-carbonyl)-pyridine-carboxylic acid (IV) and about 0.9 to 1.5 moles, preferably 1.0 to 1.2 moles of the heterocyclic compound (III) or the aniline compound (V) are added to about 3 to 30 moles of concentrated sulfuric acid, acetic anhydride or polyphosphoric acid, and the resulting mixture is allowed to react at a temperature of about 30° to 130° C for a period of from about 2 to 10 hours. The reaction product is then poured into 1 to 5 liters of ice-water to hydrolyze or dilute the condensing agent, and the resulting aqueous solution was made weakly acidic or neutral with dilute aqueous sodium hydroxide. Benzene or toluene is added thereto followed by stirring to transfer any unreacted heterocyclic compound or aniline compound to the benzene or toluene layer, which is then removed by separation. The residual aqueous layer is adjusted to a pH of about 11 to 12 with dilute aqueous sodium hydroxide and the precipitated solid is filtered, washed successively with water and a small amount of ethanol and dried to obtain in good yield a lactone color former of the pyridine-carboxylic acid represented by the formula (I) as substantially colorless of slightly colored crystals. Alternatively, the residual aqueous layer as obtained above, after removal of the benzene or toluene layer, is adjusted to a pH of 11 to 12 with dilute aqueous sodium hydroxide, and benzene or toluene is added to the resulting aqueous solution followed by stirring to transfer the lactone color former of pyridine-carboxylic acid to the benzene or toluene layer, which was then recovered by separation. Benzene or toluene was distilled off from the benzene or toluene layer. The residue was washed successively with water, a small amount of ethanol, benzene, lizroin or petroleum ether and dried. Further alternatively, the above reaction product is poured into 1 to 5 liters of ice-water to hydrohyze or dilute the condensing agent, and the resulting aqueous solution was adjusted to a pH of 11 to 12 with dilute aqueous sodium hydroxide. Benzene or toluene is added thereto followed by stirring to transfer the lactone color former of pyridine-carboxylic acid into the benzene or toluene layer which is then recovered by separation. The benzene or toluene layer is worked up in the same manner as described above. Thus, a substantially colorless or slightly colored lactone color former of pyridine-carboxylic acid represented by the formula [I] can be obtained in high yield. If necessary, the lactone color former of pyridinecarboxylic acid thus obtained can be recrystallized. The present invention, will now be illustrated by reference to the following Examples, but they are not to be construed as limiting the present invention.

EXAMPLE 1

10 g of quinolinic anhydride and 26 g of N,N-diethyl-3-ethoxyaniline were added to 100 ml of benzene, and 27 g of anhydrous aluminum chloride was added to the mixture in small portions over about 20 minutes while stirring and maintaining the temperature at 30° to 35° C. Upon completion of the addition, the mixture was allowed to react for 4 hours at a temperature in the range of from 35° to 38° C and thereafter was cooled to room temperature. The benzene was removed by decantation, and the resulting reaction product was added to 800 g of ice-water followed by stirring. The precipitated solid was filtered, washed with water and dried to give 15.5 g of an isomer mixture of 3-[4'-diethylamino-2'-ethoxy-benzoyl]-pyridine-carboxylic acid-(2) and 2-[4'-diethylamino-2'-ethoxy-benzoyl]-pyridinecarboxylic acid-(3) as pale brown crystals having a melting point of 245° to 253° C.

15.5 g of the resulting crystals was then dissolved in dilute aqueous sodium hydroxide. Dilute aqueous hydrochloric acid was added to the solution to adjust the pH to 6 and the precipitated solid was filtered (the filtrate was set aside), washed and dried to give 10 g of an isomer mixture comprising predominantly 3-[4'-diethylamino-2'-ethoxy-benzoyl]-pyridinecarboxylic acid-(2) and a small amount of 2-[4'-diethylamino-2'-ethoxy-benzoyl]-pyridine-carboxylic acid-(3) as pale brown crystals having a melting point of 293° to 297° C. 10 g of the resulting crystals was then recrystallized several times from a mixed solvent of methanol-benzene (1:1 by volume) to give 6.5 g of a highly purified 3-[4'-diethylamino-2'-ethoxy-benzoyl]-pyridine-carboxylic acid-(2) as pale yellow crystals having a melting point of 295° to 296° C.

The filtrate having a pH of 6 obtained from the filtration of the above product was then adjusted to a pH of 2 with dilute aqueous hydrochloric acid, and the precipitated solid was filtered washed with water and dried to give 4 g of an isomer mixture comprising predominantly 2-[4'-diethylamino-2'-ethoxybenzoyl]-pyridine-carboxylic acid-(3) and a small amount of 3-[4'-diethylamino-2'-ethoxy-benzoyl]-pyridine-carboxylic acid-(2) as pale brown crystals having a melting point of 176° to 181° C.

4 g of the isomer mixture thus obtained was then recrystallized several times from a mixed solvent of methanoltoluene (1:1 by volume) to give 2.3 g of a highly purified 2-[4'-diethylamino-2'-ethoxy-benzoyl[-pyridine-carboxylic acid-(3) as substantially colorless crystals having a melting point of 179 to 180° C.

2.5 g of the above obtained 3-[4'-diethylamino-2'-ethoxy-benzoyl]-pyridine-carboxylic acid-(2) (m.p., 295° – 296° C) and 1.4 g of 1-methyl-2,3,4-tetrahydroquinoline were added to 15 g of acetic anhydride, and the resulting mixture was allowed to react at a temperature of 80° to 85° C for 3 hours followed by cooling to room temperature. The reaction product was poured into 150 g of ice-water to hydrolyze the acetic anhydride while stirring. After completion of the hydrolysis, 50 ml of benzene was added to the resulting solution and the aqueous layer of the mixture was adjusted to a pH of 6.5 with dilute aqueous sodium hydroxide to transfer any unreacted 1-methyl-2,3,4-tetrahydroquinoline to the benzene layer, which was then removed by separation. The residual aqueous solution was adjusted to a pH of 12 with dilute aqueous sodium hydroxide, and the precipitated solid was filtered, washed successively with water and a small amount of ethanol and dried to give 2.3 g of 3-[α-{1'-methyl-2',-3',4'-tetrahydroquinoline (6')-yl}-α{4'-diethylamino-2'-ethoxyphenyl}-α-oxy]-methylpyridine-carboxylic acid-(2) lactone as slightly pale yellow colored crystals having a melting point of 163° to 165° C. A benzene solution of the crystals thus obtained was adsorbed on acid clay and immediately a greenish blue color developed.

2.5 g of the above obtained 2-(4'-diethylamino-2'-ethoxybenzoyl)pyridine-carboxylic acid-(3) and 1.4 g of 1-methyl-2,3,4-tetrahydroquinoline were added to 15 g of acetic anhydride, and the resulting mixture was allowed to react at a temperature of 85° to 90° C for 5 hours followed by cooling to room temperature. The reaction product was poured into 200 g of ice-water to hydrolyze the acetic anhydride while stirring. After completion of the hydrolysis, 50 ml of benzene was added to the resulting solution and the aqueous layer of the mixture was adjusted to a pH of 11 to 12 with dilute aqueous sodium hydroxide to transfer the resulting lactone color former of pyridine-carboxylic acid to the benzene layer, which was then recovered by separation. The benzene was distilled off from the benzene layer, and the residue thus obtained was washed with a small amount of petroleum ether and dried to give 2.5 g of a lactone color former of 2-[α-{1'-methyl-2',3',4'-tetrahydroquinoline-(6')-yl}-α-{4'-diethylamino-2'-ethoxyphenyl}-α-oxy]-methylpyridine-carboxylic acid-(3) as pale yellow colored crystals having a melting point of 126° to 128° C. A benzene solution of the crystals thus obtained was adsorbed on acid clay and immediately a greenish blue color developed.

EXAMPLE 2

2.5 g of the isomer mixture of pyridine-carboxylic acid having a melting point of 245° to 253° C as described in Example 1 and 2.2 g of 1-methyl-2,3,4-tetrahydroquinoline were added to 20 g of acetic anhydride, and the mixture was allowed to react at a temperature of from 85° to 95° C for 4 hours followed by cooling to room temperature. The reaction product was poured into 200 g of ice-water, to hydrolyze the acetic anhydride while stirring. After completion of the hydrolysis, the mixture was adjusted to a pH of about 11 to 12 with dilute aqueous sodium hydroxide. To the mixture was added 50 ml of benzene to transfer the resulting lactone of pyridine-carboxylic acid to the benzene layer, and the benzene layer was recovered by separation. The benzene was distilled off from the benzene layer and the residue thus obtained was washed with a small amount of petroleum ether and dried to give 2.4g of an isomer mixture of 3(and 2)-[α-{1'-methyl-2',3',4'-tetrahydroquinoline-(6')-yl}-α-{4'-diethylamino-2'-ethoxyphenyl}-α-oxy]-methyl-pyridine-carboxylic acid-2[and (3)] lactone as pale yellow colored crystals having a melting point of 141° to 147° C. A benzene solution of the resulting crystals was adsorbed on acid clay and immediately a greenish blue color developed.

EXAMPLE 3

12.0 g of quinolinic anhydride and 23.6 g of 1-methyl-2,3,4-tetrahydroquinoline were added to 120 ml of benzene, and 32.0 g of anhydrous aluminum chloride was added to the mixture in small portions over about 30 minutes while stirring and maintaining the temperature at 10° to 20° C. Upon completion of the addition, the mixture was allowed to react for 7 hours at a temperature in the range of from 30° to 40° C and thereafter was cooled to room temperature. The benzene was removed by decantation, and the resulting reaction product was added to 1200 g of ice-water followed by stirring. The precipitated solid was filtered, washed with water and dried to give 16.9 g of an isomer mixture of 3(and 2)-{1'-methyl-2',3',4'-tetrahydroquinoline-carbonyl-(6')}-pyridine-carboxylic acid-(2) [and (3)] as pale brown crystals having a melting point of 240° to 248° C. If necessary, the crystals may be recrystallized.

3.0 g of the above obtained isomer mixture of pyridine-carboxylic acid and 2.8 g of N-β-chloroethyl-N-ethylaniline were added to 20 g of acetic anhydride, and the resulting mixture was allowed to react at a temperature of 80° to 85° C for 2 hours. After completion of the reaction, the reaction product was worked up in the same manner as described in Example 2 to give 2.6 g of an isomer mixture of 3(and 2)-[α-{1'-methyl-2',3',4'-tetrahydroquinoline-(6')-yl}-α-{4'-(N-β-chloroethyl-N-ethyl)-aminophenyl}-α-oxy]-methyl-pyridine-carboxylic acid-(2) [and (3)] lactone as pale yellow colored crystals having a melting point of 93° to 98° C. A toluene solution of the crystals thus obtained was adsorbed on acid clay and immediately developed a blue color.

EXAMPLE 4

3.0 g of the isomer mixture of a pyridine-carboxylic acid (m.p., 240° – 248° C) obtained in Example 3 and 2.7 g of N-benzene-N-methylaniline were added to 20 g of acetic anhydride, and the resulting mixture was allowed to react at a temperature of 80° to 90° C for 3 hours followed by cooling to room temperature. The reaction product was poured into 200 g of ice-water to hydrolyze the acetic anhydride while stirring. After completion of the hydrolysis, 50 ml of toluene was added to the resulting solution and the aqueous layer of the mixture was adjusted to a pH of 6.5 with dilute aqueous sodium hydroxide to transfer any unreacted N-benzyl-N-methylaniline to the toluene layer, which was then removed by separation. The residual aqueous solution was adjusted to a pH of 12 with dilute aqueous sodium hydroxide, and the precipitated solid was filtered, washed successively with water and a small amount of ethanol and dried to give 3.1 g of 3-(and 2)[α-{1'-methyl-2',3',4'-tetrahydroquinoline-(6')-yl}-α-{4'-(N-benzyl-N-methyl)-aminophenyl}-α-oxy]-methylpyridine-carboxylic acid-(2) [and (3)] lactone as pale blue colored crystals having a melting point of 92° to 97° C. A toluene solution of the crystals thus obtained was adsorbed on acid clay and immediately developed a blue color.

EXAMPLE 5

22 g of N,N-dibenzylaniline was added to 60 ml of benzene, and 17 g of anhydrous aluminum chloride was added to the resulting mixture in small portions over 10 minutes while stirring at a temperature of 19° to 21° C followed by addition of 6.0 g of quinolinic anhydride in small portions over 15 minutes at a temperature of 21° to 35° C. After completion of the addition, the mixture was allowed to react at a temperature of 35° to 38° C for 5 hours followed by allowing the mixture to cool to room temperature. The reaction product was then poured into 300 g of ice-water, and 100 ml of benzene was then added to the resulting aqueous solution to transfer the reaction product to the benzene layer which was then recovered by separation. The benzene was distilled off from the benzene layer, and the residue thus obtained was dried to give 16.5 g of an isomer mixture of 3 (and 2)-(4'-dibenzylaminobenzoyl)-pyridine-carboxylic acid-(2)[and (3)] as pale brown colored crystals having a melting point of 165° to 174° C.

4.0 g of the isomer mixture of a pyridine-carboxylic acid obtained above and 2.5 g of 1-methyl-2,3,4-tetrahydroquinoline were added to 25 g of acetic anhydride and the mixture was allowed to react at a temperature of 85° to 90° C for 4 hours. After the completion of the reaction, the reaction product was worked up in the same manner as described in Example 4 to obtain 4.9 g of an isomer mixture of 3(and 2)-[α-{1'-methyl-2',3',4'-tetrahydroquinoline-(6')-yl}-α-{4'-dibenzylaminophenyl}-α-oxy]-methyl-pyridine-carboxylic acid-(2) [and (3)] lactone as pale yellow-colored crystals having a melting point of 129° to 137° C. A benzene solution of the crystals thus obtained was adsorbed on acid clay and immediately a blue color developed.

EXAMPLE 6

10.0 g of quinolinic anhydride and 12.0 g of N-phenylmorpholine were added to 150 ml of benzene, and 20.5 g of anhydrous aluminum chloride was added to the mixture in small portions over about 15 minutes while stirring and maintaining the temperature at 20° to 30° C. Upon completion of the addition, the mixture was allowed to react for 5 hours at a temperature in the range of from 35° to 40° C and thereafter was cooled to room temperature. The benzene was removed by decantation, and the resulting reaction product was added to 400 g of ice-water followed by addition of 200 ml of tetrachloroethane. The resulting mixture was stirred for 1 hour, and the tetrachloroethane layer was recovered by separation. Tetrachloroethane was distilled off from the tetrachloroethane layer, and the residue was dried to give 15.5 g of an isomer mixture of 3 (and 2)-[4'-morpholinobenzoyl]-pyridine-carboxylic acid-(2)[and (3)] as pale brown crystals having a melting point of 168° to 175° C. If necessary, these crystals may be recrystallized.

3.0 g of the isomer mixture of pyridine-carboxylic acid thus obtained and 2.1 g of 1-methyl-2,3,4-tetrahydroquinoline were added to 15 g of acetic anhydride, and the mixture was allowed to react at 90° to 95° C for 1 hour. After the reaction, the reaction product was worked up in the same manner as described in Example 2 to give 3.1 g of an isomer mixture of 3 (and 2)-[α-{4'-morpholinophenyl}-α-{1'-methyl-2', 3',4'-tetrahydroquinoline-(6')-yl}-α-oxy]-methylpyridine-carboxylic acid-(2) [and (3)] lactone as pale yellow colored crystals having a melting point of 89° to 96° C. A benzene solution of the crystals was adsorbed on acid clay and immediately developed a blue color.

EXAMPLE 7

12.0 g of quinolinic anhydride and 24.4 g of julolidine were added to 120 ml of benzene, and 33 g of anhydrous aluminum chloride was added to the mixture in small portions over about 30 minutes while stirring and maintaining the temperature at 10 to 20° C. Upon completion of the addition, the mixture was allowed to react for 3 hours at a temperature in the range of from 45° to 50° C followed by cooling to room temperature. Thereafter, the reaction product was worked up in the same manner as described in Example 3 to give 18.0 g of an isomer mixture of 3(and 2)-[julolidine-carbonyl-(6')]-pyridine-carboxylic acid-(2)[and (3)] as pale brown colored crystals having a melting point of 260° to 265° C. If necessary, these crystals may be recrystallized.

3.0 g of the isomer mixture of pyridine-carboxylic acid above obtained and 2.5 g of N,N-dimethylaniline were added to 20 g of acetic anhydride, and the resulting mixture was allowed to react at 90°to 95° C for 5 hours. The reaction product was worked up in the same manner as described in Example 2 to obtain 2.5 g of an isomer mixture of 3(and 2)-[α-{julolidin-(6')-yl}-α-{4'-dimethylaminophenyl}-α-oxy]-methylpyridine-carboxylic acid- (2)[and (3)] lactone as pale yellow colored crystals having a melting point of 121° to 126° C. A benzene solution of the crystals was adsorbed on acid clay, and a blue color was immediately formed.

EXAMPLE 8

4.0 g of quinolinic anhydride and 8.8 g of N,N-diethyl-m-toluidine were added to 50 ml of tetrachloroethane, and 10 g of anhydrous aluminum chloride was added to the mixture in small portions over 15 minutes while stirring and maintaining the mixture at a temperature of 30° to 35° C. After the completion of the addition, the resulting mixture was allowed to react for 3 hours at a temperature of from 55° to 60° C and thereafter was cooled to room temperature. After cooling, the reaction product was worked up in the same manner as described in Example 5 to give 6.0 g of an isomer mixture of 3(and 2)-4'-diethylamino-2'-methylbenzoyl)-pyridine-carboxylic acid-(2)[and (3)] as pale brown colored crystals having a melting point of 193° to 196° C.

4.0 g of the above obtained isomer mixture of pyridine-carboxylic acid and 2.7 g of 1-methyl-2,3,4-tetrahydroquinoline were added to 20 g of acetic anhydride and the mixture was allowed to react at a temperature of 80° to 85° C for 3 hours. The reaction product was worked up in the same manner as described in Example 2 to give 4.9 g of an isomer mixture comprising 3(and 2)-[α-{4'-diethylamino-2'-methylphenyl}-α-{1'-methyl-2',3',4'-tetrahydroquinoline-(6')-yl}-α-oxy]-methylpyridine-carboxylic acid-(2) [and (3)] lactone as pale yellow colored crystals having a melting point of 132° to 136° C. A toluene solution of the crystals was absorbed on acid clay and immediately a bluish green color developed.

EXAMPLE 9

10 g of quinolinic anhydride and 25 g of 9-ethylcarbazole were added to 100 ml of benzene, and 27 g of anhydrous aluminum chloride was added to the mixture in small portions at a temperature of 10° to 20° C over about 40 minutes while stirring. After the completion of addition, the mixture was allowed to react at a temperature of 40° to 50° C for 3 hours. The reaction product was worked up in the same manner as described in Example 5 to give 16.0 g of an isomer mixture of 3(and 2)-[9'-ethylcarbazole-carbonyl-(3')]-pyridine-carboxylic acid-(2)[and (3)] as pale brown colored crystals having a melting point of 155° to 167° C.

3.7 g of the isomer mixture of pyridine-carboxylic acid thus obtained and 2.1 g of N,N-dimethylaniline were added to 20 g of acetic anhydride, and the mixture was allowed to react at a temperature of 90° to 95° C for 6 hours. The reaction product was worked up in the same manner as described in Example 4 to give 1.4 g of an isomer mixture of 3(and 2)-[α-{9'-ethylcarbazol-(3')-yl}-α-{4'-dimethylaminophenyl}-α-oxy]-methylpyridine-carboxylic acid-(2)[and (3)] lactone as pale yellow colored crystals having a melting point of 186° to 195° C. A benzene solution of the thus obtained crystals was adsorbed on acid clay and immediately a purplish blue color was developed.

EXAMPLE 10

3.0 g of quinolinic anhydride and 7.0 g of acridine were added to 40 ml of tetrachloroethane, and 8.0 g of anhydrous aluminum chloride was added to the mixture in small portions over about 30 minutes at a temperature of 15° to 25° C while stirring. After the completion of the addition, the mixture was allowed to react at a temperature of 30° to 40° C for 9 hours followed by cooling to room temperature. The reaction product was worked up in the same manner as described in Example 5 to give 5.6 g of an isomer mixture comprising 3(and 2)-[acridinecarbonyl-(2')]-pyridine-carboxylic acid-(2)[and (3)] as pale brown colored crystals having a melting point of 232° to 238° C. If desired, the crystals can be recrystallized.

3.3 g of the isomer mixture of the pyridine-carboxylic acid above obtained and 2.3 g of N-benzyl-N-methylaniline were added to 25 g of acetic anhydride and the mixture was allowed to react at a temperature of 90° to 95° C for 7 hours. After the completion of the reaction, the reaction product was worked up in the same manner as described in Example 4 to give 1.5 g of an isomer mixture of 3(and 2)-[α{acridin-(2')-yl}-α-{4'-(N-benzyl-N-methyl)-aminophenyl}-α-oxy]-methylpyridine-carboxylic acid-(2)[and (3)] lactone as pale brown colored crystals. A benzene solution of the crystals was adsorbed on acid clay and immediately a purplish blue color developed.

EXAMPLE 11

5.8 g of quinolinic anhydride and 8.0 g of phenothiazine were added to 60 ml of benzene, and 8.2 g of anhydrous aluminum chloride was added to the mixture in small portions over 30 minutes while stirring and maintaining at a temperature of 15 to 25° C. After the completion of the addition, the mixture was allowed to react at a temperature of 40° to 50° C for 5 hours followed by cooling to room temperature. After cooling, the reaction product was worked up in the same manner as described in Example 5 to give 4.8 g of an isomer mixture of 3(and 2)-[phenothiazine-carbonyl-(3')]-pyridine-carboxylic acid-(2)[and (3)] as pale brown colored crystals.

2.6 g of the above obtained isomer mixture of a pyridine-carboxylic acid and 1.4 g of N-methyldiphenylamine were added to 20 g of acetic anhydride and the mixture was allowed to react at a temperature of 95° to 100° C for 6 hours. After the completion of the reaction, the reaction product was then worked up in the same manner as described in Example 4 to give 1.3 g of an isomer mixture of 3(and 2)-[α-{10'-acetylphenothiazin-(3')-yl}-α-{4'-(N-methyl-N-phenyl)-aminophenyl}-α-oxy]-methylpyridinecarboxylic acid-(2)[and (3)] lactone as pale yellow colored crystals. A chloroform solution of the thus obtained crystals was adsorbed on acid clay and immediately a purplish blue color developed.

EXAMPLE 12

3.3 g of quinolinic anhydride and 4.7 g of 10 methyl-phenothiazine were added to 25 ml of benzene, and 8.7 g of anhydrous aluminum chloride was added to the mixture in small portions over about 40 minutes while stirring and maintaining at a temperature of 15° to 25° C. After the completion of the addition, the mixture was allowed to react at a temperature of 40° to 45° C for 3 hours followed by cooling to room temperature. After cooling, the reaction product was worked up in the same manner as described in Example 5 to give 6.5 g of an isomer mixture of 3 (and 2)-[10'-methylphenothiazine-carbonyl-(3')]-pyridine-carboxylic acid-(2)[and (3)] as pale brown colored crystals having a melting point of 148° to 153° C.

3.7 g of the isomer mixture of pyridine-carboxylic acid above obtained and 2.4 g of N,N-diethyl-3-chloroaniline were added to 30 g of concentrated sulfuric acid, and the mixture was allowed to react at 60° to 70° C for 5 hours followed by cooling to room temperature. The reaction product was then worked up in the same manner as described in Example 4 to give 2.1 g of an isomer mixture of 3(and 2)-[α-{10'-methylphenothiazin-(3')-yl}-α-{2'-chloro-4'-diethylaminophenyl}-α-oxy]-methylpyridine-carboxylic acid-(2)[and (3)] lactone as pale brown colored crystals. A toluene solution of the crystals was adsorbed on acid clay and immediately a purplish blue color developed.

EXAMPLE 13

6.0 g of quinolinic anhydride and 6.0 g of thiophene were added to 20 ml of tetrachloroethane, and 13 g of anhydrous aluminum chloride was added to the mixture in small portions over about 30 minutes while stirring and maintaining at a temperature of 10° to 20° C. After completion of addition, the mixture was allowed to react at a temperature of 40 to 45° C for 6 hours and thereafter cooled to room temperature. After cooling, the reaction product was then worked up in the same manner as described in Example 5 to give 6.6 g of an isomer mixture of 3(and 2)-[2'-thenoyl]-pyridine-carboxylic acid-(2)[and (3)] as pale yellow colored crystals having a melting point of 135° to 143° C.

4.7 g of the above obtained isomer mixture of a pyridine-carboxylic acid and 4.1 g of N-methyl-N-4'-ethoxyphenylaniline were added to 30 g of acetic anhydride and the mixture was allowed to react at a temperature of 100° to 105° C for 5 hours. After completion of the reaction, the reaction product was then worked up in the same manner as described in Example 4 to give 3.7 g of an isomer mixture of 3(and 2)-[α-{thiophen-(2')-yl}-α-{4'-(N-methyl-N-4''-ethoxyphenyl)-aminophenyl}-α-oxy]-methylpyridine-carboxylic acid-(2)[and (3)] lactone as pale yellow colored crystals. A benzene solution of the crystals was adsorbed on acid clay and immediately a purple color developed.

EXAMPLE 14

3.0 g of quinolinic anhydride and 5.4 g of thianaphthane were added to 30 ml of benzene, and 8.0 g of anhydrous aluminum chloride was added to the mixture in small portions at a temperature of 10° to 20° C over about 30 minutes while stirring. After the completion of the addition, the mixture was allowed to react at a temperature of 30° to 35° C for 9 hours followed by cooling to 20° C. After cooling, the reaction product was worked up in the same manner as described in Example 5 to give 4.4 g of an isomer mixture of 3(and 2)-[thianaphthene-carbonyl-(2')]-pyridine-carboxylic acid-(2)[and (3)] as pale brown colored crystals having a melting point of 124° to 131° C.

2.4 g of the above obtained isomer mixture of pyridine-carboxylic acid and 1.6 g of N-acetonylamiline were added to 30g of acetic anhydride and the mixture was allowed to react at a temperature of 120° to 125° C for 3 hours. After the completion of the reaction, the reaction product was worked up in the same manner as described in Example 4 to give 3.7 g of an isomer mixture of 3(and 2)-[α-{thianaphthen-(2')-yl}-α-{4'-acetonylaminophenyl}-α-oxy]-methylpyridine-carboxylic acid-(2)[and (3)] lactone as pale yellow colored crystals. A toluene solution of the crystals was adsorbed on acid clay and immediately a reddish purple color developed.

EXAMPLE 15

6.0 g of quinolinic anhydride and 18.0 g of N-benzyl-N-ethyl-toluidine were added to 50 ml of tetrachloroethane, and 16.2 g of anhydrous aluminum chloride was added to the mixture in small portions over about 15 minutes while stirring and maintaining at a temperature of 25° to 35° C. After completion of addition, the mixture was allowed to react at a temperature of 35° to 38° C for 4 hours followed by cooling to room temperature. After cooling, the reaction product was worked up in the same manner as described in Example 5 to give 14.5 g of an isomer mixture of 3(and 2)-[4'-(N-benzyl-N-ethyl)-amino-2'-methylbenzoyl]-pyridine-carboxylic acid-(2)[and (3)] as pale yellowish brown colored crystals having a melting point of 245° to 249° C.

4.0 g of the isomer mixture of pyridine-carboxylic acid above obtained and 4.3 g of 3-dimethylamino-10-methylphenothiazine were added to 30 g of acetic anhydride, and the mixture was allowed to react at 110° to 120° C for 4 hours. After completion of the reaction, the reaction product was worked up in the same manner as described in Example 4 to give 2.9 g of an isomer mixture of 3(and 2)-[α-{4'-(N-benzyl-N-ethyl)-amino-2'-methylphenyl}-α-{7'-dimethylamino-10'-ethylphenothiazine-(3')-yl}-α-oxy]-methylpyridine-carboxylic acid-(2)[and (3)] lactone as pale blue colored crystals. A tetrachloroethane solution of the crystals was adsorbed on acid clay and immediately a blue color developed.

EXAMPLE 16

5.0 g of quniolinic anhydride and 5.5 g of N-methylaniline were added to 50 ml of tetrachloroethane, and 13.5 g of anhydrous aluminum chloride was added to the mixture in small portions over 20 minutes while stirring and maintaining at a temperature of 20° to 35° C. After completion of the addition, the mixture was allowed to react at 35° to 40° C for 4 hours and the reaction product was worked up in the same manner as described in Example 5 to give 6.0 g of an isomer mixture of 3(and 2)-(4'-methylaminobenzoyl)-pyridine-carboxylic acid-(2)[and (3)] as pale brown colored crystals having a melting point of 138° to 145° C.

2.0 g of the isomer mixture of pyridine-carboxylic acid above obtained and 2.9 g of 3-nitro-9-ethylcarbazole were added to 30 g of concentrated sulfuric acid, and the mixture was allowed to react at 70° to 80° C for 4 hours followed by cooling to room temperature. The reaction product was then worked up in the same manner as described in Example 4 to give 1.1 g of an isomer mixture of 3(and 2)-[α-{4'-methylaminophenyl}-α-{6'-nitro-9'-ethylcarbazol-(3')-yl}-α-oxy]-methylpyridine-carboxylic acid-(2)[and (3)] lactone as pale brown colored crystals. A chloroform solution of the crystals was adsorbed on acid clay and immediately a reddish purple color developed.

EXAMPLE 17

4.0 g of quinolinic anhydride and 5.4 g of acetanilide were added to 30 ml of tetrachloroethane, and 10.5 g of anhydrous aluminum chloride was added to the mixture in small portions over 15 minutes while stirring and maintaining at a temperature of 20° to 35° C. After completion of the addition, the mixture was allowed to react at 50° to 55° C for 4 hours and the reaction product was worked up in the same manner as described in Example 3 to give 5.0 g of an isomer mixture of 3(and 2)-(4'-acetamidebenzoyl)-pyridine-carboxylic acid-(2)[and (3)] as pale brown colored crystals having a melting point of 146° to 157° C.

2.0 g of the isomer mixture of pyridine-carboxylic acid above obtained and 3.8 g of 10-acetylphenothiazine were added to 30 g of acetic anhydride, and the mixture was allowed to react at 110° to 120° C for 7 hours followed by cooling to room temperature. The reaction product was then worked up in the same manner as described in Example 4 to give 0.9 g of an isomer mixture of 3(and 2)-[α-{4'-acetamidophenyl}-α-{10'-acetylphenothiazin(3')-yl}-α-oxy]-methylpyridine-carboxylic acid-(2)[and (3)] lactone as pale yellow colored crystals. A tetrachloroethane solution of the crystals was adsorbed on acid clay and immediately a red color developed.

0.6 g of the isomer mixture of lactones above obtained was dissolved in tetrachloroethanem and an ethanol-dilute hydrochloric acid aqueous solution was added thereto, The resulting mixture was allowed to react at reflux for 3 hours followed by distilling off the solvent under reduced pressure. The residue was taken into benzene and the aqueous layer of the resulting solution was adjusted to a pH of about 11 with dilute aqueous sodium hydroxide. The benzene layer was recovered, and the benzene was distilled off from the benzene layer. The residue was washed with a small amount of petroleum ether and dried to obtain 0.2 g of an isomer mixture of 3(and 2)-[α-{4'-aminophenyl}-α-{phenothiazin-(3')-yl}-α-oxy]-methylpyridine-carboxylic acid-(2) [and (3)] lactone as pale brown colored crystals. A toluene solution of the crystals was adsorbed on acid clay and immediately a red color developed.

EXAMPLE 18

6.0 g of quinolinic anhydride and 15.0 g of N-methylN-(4'-methylphenyl)-aniline were added to 50 ml of benzene, and 16.2 g of anhydrous aluminum chloride was added to the mixture in small portions over 20 minutes while stirring and maintaining at a temperature of 30° to 50° C. After completion of the addition, the mixture was allowed to react at 50° to 55° C for 4 hours and the reaction product was worked up in the same manner as described in Example 3 to give 9.0 g of an isomer mixture of 3(and 2)-[4'-(N-4''-methylphenyl-N-methyl)-aminobenzoyl]-pyridine-carboxylic acid-(2)[and (3)] as pale brown colored crystals having a melting point of 177° to 186° C.

3.0 g of the above obtained isomer mixture of pyridine-carboxylic acid compounds and 2.1 g of julolidine were added to 30 g of polyphosphoric acid, and the mixture was allowed to react at a temperature of 90° to 100° C for 2 hours. After the completion of the reaction, the reaction product was worked up in the same manner as described in Example 4 to give 3.4 g of an isomer mixture of 3 (and 2)-[α-{4'-(N-4''-methylphenyl-N-methyl)-aminophenyl}-α-{julolidin-(6')-yl}-α-oxy]-methylpyridine-carboxylic acid-(2) [and (3)] lactone as pale yellow colored crystals. A toluene solution of the crystals was adsorbed on acid clay and immediately a greenish blue color developed.

EXAMPLE 19

A quinolinic anhydride and an aniline compound or a heterocyclic compound were reacted and the reaction product was worked up in the same manner as described in Examples 1, 3 and 5 to 18 to prepare the corresponding isomer mixture of pyridine-carboxylic acid. The resulting isomer mixture and a heterocyclic compound or an aniline compound were reacted and worked up in the same manner as described in Examples 2 and 3 to 18 to obtain the corresponding isomer mixture of pyridine-carboxylic acid lactones. The corresponding pyriidne-carboxylic acids, and heterocyclic compounds or aniline compounds and amounts thereof used in this example and the melting points and crystal appearance of the resulting pyridine-carboxylic acid lactones together with colors developed on acid clay are shown in Table below.

| Lactone Color Former No. | Pyridine-Carboxylic Acid (II) or (IV) and Amount Used (g) | Heterocyclic Compound (III) or Aniline Compound (V) and Amount Used (g) | Lactone Color Former (I) | | |
|---|---|---|---|---|---|
| | | | Yield (g) | Crystal Appearance | Color Developed on Acid Clay |
| 19–1 | 3-(and 2) [α-{1'-Methyl-2',3',4'-tetrahydroquinoline carbonyl-(6')]-pyridine-carboxylic acid-(2) [and (3)]  3.0 | N,N-Diethyl-3-chloroaniline  2.6 | 3(and 2)-[α-{1'-Methyl-2',3',4'-tetrahydroquinoline-(6')-yl}-α-{4'-(N,N-diethyl)-amino-2'-chlorophenyl}-α-oxy]-methylpyridine-carboxylic acid-(2) [and (3)] lactone  1.4 | pale yellow | blue |
| 19–2 | " 3.0 | N-Ethyl-N-β-ethoxyethyl-3-methylaniline  2.7 | 3(and 2)-[α-{1'-Methyl-2',3',4'-tetrahydroquinoline-(6')-yl}-α-{4'-(N-ethyl-N-β-ethoxyethyl)-amino-2-methylphenyl}-α-oxy]-methylpyridine-carboxylic acid-(2) [and (3)] lactone  3.2 | pale blue | greenish blue |
| 19–3 | " 3.0 | N-β-Diethylaminoethylaniline  2.5 | 3(and 2)-[α-{1'-Methyl-2',3',4'-tetrahydroquinoline-(6')-yl}-α-{4'-(Nβ-diethylaminoethyl)-aminophenyl}-α-oxy]-methylpyridine-carboxylic acid-(2) [and (3)] lactone  2.4 | pale yellow | blue |
| | 3(and 2)-{1'-methyl-2',3',4'-tetrahydroquinoline-carbonyl-(6')}- | N,N-dimethyl-3-methoxy-aniline | 3(and 2)-[α-{1'-Methyl-2',3',4'-tetrahydroquinoline-(6')-yl}-α-{4'-dimethylamino-2'-methoxyphenyl}- | | |

-continued

| Lactone Color Former No. | Pyridine-Carboxylic Acid (II) or (IV) and Amount Used (g) | Heterocyclic Compound (III) or Aniline Compound (V) and Amount Used (g) | Lactone Color Former (I) Yield (g) | Crystal Appearance | Color Developed on Acid Clay |
|---|---|---|---|---|---|
| 19-4 | 3-chloropyridine-carboxylic acid-(2)[and (3)] 3.0 | N,N-Diethyl-3-nitroaniline 2.3 | 3.3 | pale blue | bluish green |
| | 3(and 2)-{1'-Methyl-2',3',4'-tetrahydroquinone-carbonyl-(6')}-3-methylpyridine-carboxylic acid-(2)[and (3)] 3.0 | | 3(and 2)-[α-{1'-Methyl-2',3',4'-tetrahydroquinone-(6')-yl}-α-{4'-diethylamino-2'-nitrophenyl}-α-oxy]-methyl-4-methylpyridine-carboxylic acid-(2)[and (3)] lactone | | |
| 19-5 | | N,N-Dimethylaniline 2.6 | 0.4 3(and 2)-[α-{1'-Methyl-2',3',4'-tetrahydroquinoline-(6')-yl}-α-{4'-dimethylaminophenyl}-α-oxy]-methyl-6-phenylpyridine-carboxylic acid-(2)[and (3)] lactone | pale yellow | purple |
| 19-6 | 2-phenylpyridine-carboxylic acid-(2)[and (3)] 3.0 | N-Methyl-N-4'-methylphenyl-aniline 2.1 | 0.9 3(and 2)-[α-{1'-Methyl-2',3',4'-tetrahydroquinoline-(6')-yl}-α-{(4'-(N-methyl-N-4''-methylphenyl)-aminophenyl}-α-oxy]-methylpyridine-carboxylic acid-(2)[and (3)] lactone | pale brown | blue |
| 19-7 | 3(and 2)-{1'-Methyl-2',3',4'-tetrahydroquinone-carbonyl-(6')}-pyridine-carboxylic acid-(2)[and (3)] 3.0 | N-β-Oxylethyl-N-β-cyanoethyl-aniline 2.7 | 2.1 3(and 2)-[α-{1'-Methyl-2',3',4'-tetrahydroquinoline-(6')-yl}-α-{4'-(N-β-hydroxyethyl-N-β-cyanoethyl)-aminophenyl}-α-oxy]-methylpyridine-carboxylic acid-(2)[and (3)] lactone | pale blue | bluish green |
| 19-8 | " 3.0 | N-Benzoylaniline 2.6 | 1.3 3(and 2)-[α-{1'-Methyl-2',3',4'-tetrahydroquinoline-(6')-yl}-α-{4'-benzoylamidophenyl}-α-oxy]-methyl pyridine-carboxylic acid-(2)[and (3)] lactone | pale blue | blue |
| 19-9 | 3(and 2)-{Julolidine-carbonyl-(6')-}-pyridine-carboxylic acid-(2)[and (3)] 3.0 | N-Methyl-N-4'-chlorophenyl-aniline 2.4 | 0.4 3(and 2)-[α-{Julolidin-(6')-yl}-α-{4'-(N-4''-chlorophenyl-N-methyl)-aminophenyl}-α-oxy]-methylpyridine-carboxylic acid-(2)[and (3)] lactone | pale brown | purple |
| 19-10 | | 4,4'-bis-Dimethylamino-phenylmethane 2.4 | 1.3 3(and 2)-[α-{Julolidin(6')-yl}-α-{4'-dimethylamino-2'-(4''-dimethylamino)-benzylphenyl}-α-oxy]-methylpyridine-carboxylic acid-(2)[and (3)] lactone | pale yellow | blue |
| 19-11 | " 3.0 | N-Ethyl-N-4'-nitrobenzyl-aniline 3.4 | 1.9 3(and 2)-[α-{Julolidin-(6')-yl}-β-{4'-(N-ethyl-N-4''-nitrobenzyl)-aminophenyl}-α-oxy]-methyl-pyridine-carboxylic acid-(2)[and (3)] lactone | pale green | bluish green |
| 19-12 | " 3.0 | N,N-Dimethyl-3-(4'-chloro)-phenoxyaniline 3.1 | 1.3 3(and 2)-[α-{Julolidin-(6')-yl}-α-{4'-dimethylamino-2'-(4''-chlorophenoxy)-phenyl}-α-oxy]-methylpyridine-carboxylic acid-(2)[and (3)] lactone | pale brown | purplish blue |
| 19-13 | 3(and 2)-{Julolidine-carbonyl-(6')-}-pyridine-carboxylic acid-(2)[and (3)] 3.0 | N,N-Dimethyl-3-(4'-methyl)-benzyloxyaniline 2.5 | 2.1 3(and 2)-[α-{Julolidin-(6')-yl}-α-{4'-dimethylamino-2'-(4''-methyl)-benzyloxyphenyl}-α-oxy]-methylpyridine-carboxylic acid-(2)[and(3)] lactone | pale green | green |
| 19-14 | " 3.0 | Thionaphthene 2.9 | 2.3 3(and 2)-[α-{4'-(Pyrrolidin-(1'')-yl)-phenyl}-α-{thionaphthen-(2')-yl}-α-oxy]-methylpyridine-carboxylic acid-(2)[and (3)] lactone | pale green | green |
| 19-15 | 3(and 2)-[4'-{Pyrrolidin-(1'')-yl}-benzoyl]-pyridine-carboxylic acid-(2)[and (3)] 2.5 | 1-Methyl-2,3,4-tetrahydroquinoline 1.7 | 2.5 3(and 2)-[α-{1'-Methyl-2',3',4'-tetrahydroquinoline-(6')-yl}-α-{4'-(piperazin-(1'')-yl)-phenyl}-α-oxy]-methylpyridine-carboxylic acid-(2)[and (3)] lactone | pale yellow | purple |
| 19-16 | 3(and 2)-[4'-{Piperazin-(1'')-yl}-benzoyl]-pyridine-carboxylic acid-(2)[and (3)] 2.5 | Julolidine 1.7 | 2.8 3(and 2)-[α{Julolidin-(6')-yl}-α-{4'-piperidino-phenyl}-α-oxy]-methylpyridine-carboxylic acid-(2)[and (3)] lactone | pale yellow | bluish purple |
| 19-17 | 3(and 2)-(4'-Piperidinobenzoyl)-pyridine-carboxylic acid-(2)[and (3)] 2.5 | 1.9 | 3.1 | pale yellow | blue |

-continued

| Lactone Color Former No. | Pyridine-Carboxylic Acid (II) or (IV) and Amount Used (g) | Heterocyclic Compound (III) or Aniline Compound (V) and Amount Used (g) | Yield (g) | Crystal Appearance | Color Developed on Acid Clay |
|---|---|---|---|---|---|
| 19-18 | 3(and 2)-(4'-Diethylamino-2'-methylaminobenzoyl)-pyridine-carboxylic acid-(2)[and (3)] 2.0 | Thionaphthene 0.8 | 1.9 | 3(and 2)-[α-{4'-Diethylamino-2'-methylaminophenyl}-{thionaphthen-2'-yl}-α-oxy]-methylpyridine-carboxylic acid-(2)[and (3)] lactone pale brown | greenish blue |
| 19-19 | 3(and 2)-{4'-(N-Phenoxyethyl-N-ethyl)-amino-2'-methylbenzoyl}-pyridine-carboxylic acid-(2) 3.0 | Thiophene 0.9 | 2.7 | 3(and 2)-[α-{4'-(N-Phenoxyethyl-N-ethyl)-amino-2'-methylphenyl}-α-{thiophen-(2')-yl}-α-oxy]-methyl-pyridine-carboxylic acid-(2)[and (3)] lactone pale yellow | blue |
| 19-20 | 3(and 2)-{4'-Dimethylamino-2'-(4''-dimethylamino)-benzyl-benzoyl}-pyridine-carboxylic acid-(2)[and (3)] 3.0 | Julolidine 1.8 | 3.7 | 3(and 2)-[α-{Julolidin-(6')-yl}-α-{4'-dimethylamino-2'-(4''-dimethylamino)benzylphenyl}-α-oxy]-methyl-pyridine-carboxylic acid-(2)[and (3)] lactone pale blue | blue |
| 19-21 | 3(and 2)-{4'-Diethylamino-2'-(4''-methyl)-benzylbenzoyl}-pyridine-carboxylic acid-(2) [and (3)] 3.0 | 1-Methyl-2,3,4-tetrahydroquinoline 1.6 | 3.2 | 3(and 2)-[α-{1'-Methyl-2',3',4'-tetrahydroquinoline-(6')-yl}-α-{4'-diethylamino-2'-(4''-methyl)-benzyl-phenyl}-α-oxy]-methylpyridine-carboxylic acid-(2) [and (3)] lactone pale yellow | blue |
| 19-22 | 3(and 2)-(4'-Diethylamino-2'-methoxymethylbenzoyl)-pyridine-carboxylic acid-(2)[and (3)] 2.5 | 9-Ethylcarbazole 1.9 | 2.1 | 3(and 2)-[α-{9'-Ethylcarbazol-(3')-yl}-α-{4'-diethylamino-2'-methoxymethylphenyl}-α-oxy]-methylpyridine-carboxylic acid-(2)[and (3)] lactone pale yellow | blue |
| 19-23 | 3(and 2)-{4'(N-Dimethylamino-phenyl-N-methyl)-benzoyl}-pyridine-carboxylic acid-(2) [and (3)] 3.0 | Julolidine 1.9 | 3.5 | 3(and 2)-[α-{Julolidin-(6')-yl}-α-{4'-N-4''-dimethylaminophenyl-N-methyl)-aminophenyl}-α-oxy]-methylpyridine-carboxylic acid-(2)[and (3)] lactone pale green | green |
| 19-24 | 3(and 2)-{4'(N-4''-dimethylamino-benzyl-N-methyl)-aminobenzoyl}-pyridine-carboxylic acid-(2) [and (3)] 3.0 | 1-Methyl-2,3,4-tetrahydroquinoline 1.4 | 3.1 | 3(and 2)-[α-{1'-Methyl-2',3',4'-tetrahydroquinoline-(6')-yl}-α-{4'-(N-4''-dimethylaminobenzyl-N-methyl)-aminophenyl}-α-oxy]-methylpyridine-carboxylic acid-(2)[and (3)] lactone pale yellow | greenish blue |
| 19-25 | 3(and 2)-(4'-Morpholinobenzoyl)-pyridine-carboxylic acid-(2) [and (3)] 2.5 | N-Phenylmorpholine 1.5 | 3.1 | 3(and 2)-[α,α-bis(4'-Morpholinophenyl)-α-oxy]-methylpyridine-carboxylic acid-(2)[and (3)] lactone pale yellow | blue |

While the invention has been described in detail and with reference to specific embodiments thereof, it will be apparent to one skilled in the art that various changes and modifications can be made therein without departing from the spirit and scope thereof.

What is claimed is:

1. A lactone compound of a pyridine-carboxylic acid represented by the formula

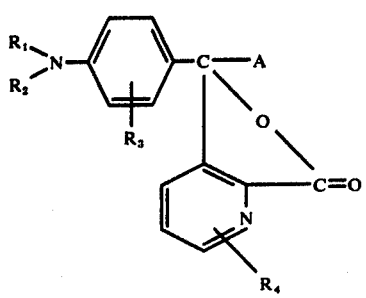

or

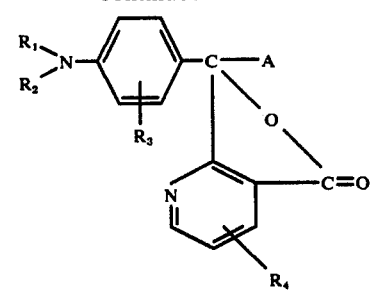

or a mixture thereof, wherein $R_1$ and $R_2$ each represents a hydrogen atom, an acetyl group, a lower alkyl group which may be substituted with a halogen atom, a cyano, hydroxyl, lower alkoxy, lower alkylamino, acetyl or phenoxy group, or a benzyl or phenyl group which may be substituted with a lower alkyl group, a halogen atom, a lower alkoxy, nitro, amino or lower alkylamino group, or $R_1$ and $R_2$ may combine to form a heterocyclic ring selected from the group consisting of morpholine, piperazine, piperidine and pyrrolidin-(1);

R₃ represents a hydrogen or halogen atom, a nitro, amino, lower alkylamino group or a lower alkyl group which may be substituted with a halogen atom or a lower alkoxy group, a lower alkoxy group which may be substituted with a halogen atom, or a benzyl, benzyloxy or phenoxy group which may be substituted with a halogen atom, a lower alkyl, alkoxy or lower alkylamino group; R₄ represents a hydrogen or halogen atom, a lower alkyl group or a phenyl group; and A represents a julolidinyl or tetrahydroquinolyl group which may be substituted with a lower alkyl, lower alkylamino, acyl or nitro group; the alkyl moiety in said lower alkyl, lower alkoxy or lower alkylamino group having 1 to 5 carbon atoms.

2. An isomer mixture of claim 1, 3(and 2)-[α-{1'-methyl-2',4'-tetrahydroquinolin-(6')-yl}-α-{4'-diethylamino-2'-ethoxyphenyl}-α-oxy]-methylpyridinecarboxylic acid-2[and (3)] lactone.

3. The lactone of claim 1 wherein said tetrahydroquinolyl group is attached to the lactone at the 6 - position and said julolidinyl group is attached to the lactone at the 6 -position.

* * * * *